United States Patent

Crawley et al.

[11] Patent Number: 5,302,594
[45] Date of Patent: Apr. 12, 1994

[54] 5-LIPOXYGENASE INHIBITORS QUINOXALINYL DERIVATIVES

[75] Inventors: Graham C. Crawley, Macclesfield; Philip N. Edwards, Bramhall, both of England

[73] Assignees: Imperial Chemical Industries PLC, London, England; ICI Pharma, Cergy Cedex, France

[21] Appl. No.: 14,673

[22] Filed: Feb. 8, 1993

Related U.S. Application Data

[62] Division of Ser. No. 584,944, Sep. 21, 1990.

[30] Foreign Application Priority Data

Sep. 29, 1989 [EP] European Pat. Off. .......... 894026996
May 2, 1990 [EP] European Pat. Off. .......... 904011830

[51] Int. Cl.$^5$ .................. A61K 31/495; C07D 241/36
[52] U.S. Cl. ..................... 514/249; 544/353; 544/354; 544/355; 544/356
[58] Field of Search ............... 514/249; 544/353, 354, 544/355, 356

[56] References Cited

U.S. PATENT DOCUMENTS

| | | | |
|---|---|---|---|
| 3,661,917 | 5/1972 | Kaiser et al. | 546/232 |
| 3,743,737 | 7/1973 | Kaiser et al. | 514/331 |
| 4,427,680 | 1/1984 | Friebe et al. | 514/314 |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1988 | Chakraborty et al. | 514/442 |
| 4,728,668 | 3/1988 | Charkraborty et al. | 514/464 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/157 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |

FOREIGN PATENT DOCUMENTS

| | | |
|---|---|---|
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 6/1989 | European Pat. Off. . |
| 1445591 | 6/1963 | Fed. Rep. of Germany ...... 546/157 |

*Primary Examiner*—Mukund J. Shah
*Assistant Examiner*—Y. N. Gupta
*Attorney, Agent, or Firm*—Cushman, Darby & Cushman

[57] ABSTRACT

The invention concerns a heterocyclic derivative of the formula I $$Q-X^1-Ar-\underset{\underset{R^3}{|}}{\overset{\overset{OR^1}{|}}{C}}-R^2 \qquad I$$

wherein

Q is an optionally substituted quinoxalinyl or a hydrogenated derivative thereof $X^1$ is oxy, thio, sulphinyl, sulphonyl or imino;

Ar is phenylene which may optionally bear one or two substituents or Ar is an optionally substituted 6-membered heterocyclene moiety containing up to three nitrogen atoms;

$R^1$ is (1-6C)alkyl, (3-6C)alkenyl or (3-6C)alkynyl; and $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is (1-4C)alkylene and $X^2$ is oxy, thio, sulphinyl, sulphonyl or imino;

or a pharmaceutically-acceptable salt thereof.

The compounds of the invention are inhibitors of the enzyme 5-lipoxygenase.

8 Claims, No Drawings

5-LIPOXYGENASE INHIBITORS QUINOXALINYL DERIVATIVES

This is a division of application Ser. No. 07/584,944, filed Sep. 21, 1990.

This invention concerns novel heterocyclic derivatives and more particularly novel heterocyclic derivatives which are inhibitors of the enzyme 5-lipoxygenase (hereinafter referred to as 5-LO). The invention also concerns processes for the manufacture of said heterocyclic derivatives and novel pharmaceutical compositions containing said heterocyclic derivatives. Also included in the invention is the use of said heterocyclic derivatives in the treatment of various inflammatory and/or allergic diseases in which the direct or indirect products of 5-LO catalysed oxidation of arachidonic acid are involved, and the production of new medicaments for such use.

As stated above the heterocyclic derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandis and thromboxanes, arise via the action of the enzyme cyclooxygenase on arachidonic acid.

We have now discovered that certain heterocyclic derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a heterocyclic derivative of the formula I (set out hereinafter) wherein Q is a 6-membered monocyclic or 10-membered bicyclic heterocyclic moiety containing one or two nitrogen atoms which may optionally bear one, two or three substituents selected from halogeno, hydroxy, oxo, carboxy, cyano, amino, (1–4C)alkyl, (1–4C)alkoxy, fluoro-(1–4C)alkyl, (1–4C)alkylamino, di-[(1–4C)alkyl]amino, hydroxy-(1–4C)alkyl, amino(1–4C)alkyl, (1–4C)alkylamino-(1–4C)alkyl, di-[(1–4C)alkyl]amino(-1–4C)alkyl, amino-(2–4C)alkoxy, (1–4C)alkylamino-(2–4C)alkoxy and di-[(1–4C)alkyl]amino-(2–4C)alkoxy; wherein $X^1$ is oxy, thio, sulphinyl, sulphonyl or imino; wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or Ar is a 6-membered heterocyclene moiety containing up to three nitrogen atoms which may optionally bear one or two substituents selected from halogeno, hydroxy, amino, (1–4C)alkyl or (1–4C)alkoxy; wherein $R^1$ is (1–6C)alkyl, (3–6C)alkenyl or (3–6C)alkynyl; and wherein $R^2$ and $R^3$ together form a group of the formula $-A^2-X^2-A^3-$ which, together with the carbon atom to which $A^2$ and $A^3$ are attached, defines a ring having 4 to 7 ring atoms, wherein $A^2$ and $A^3$, which may be the same or different, each is (1–4C)alkylene and $X^2$ is oxy, thio, sulphinyl, sulphonyl or imino, and which ring may bear one, two or three substituents, which may be the same or different, selected from halogeno, hydroxy, (1–4C)alkyl, (1–4C)alkoxy and fluoro-(1–4C)alkyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing or chemical name presented herein may represent only one of the possible tautomeric forms, the invention includes in its definition any tautomeric form of a compound of the formula I which possesses the property of inhibiting 5-LO and is not to be limited merely to any one tautomeric form named or utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for Q when it is a 6-membered monocyclic or 10-membered bicyclic heterocyclic moiety containing one or two nitrogen atoms is, for example, pyridyl, pyridazinyl, pyrimidinyl, pyrazinyl, quinolyl, isoquinolyl, cinnolinyl, quinazolinyl, quinoxalinyl, phthalazinyl or naphthyridinyl, or a hydrogenated derivative thereof such as, for example, 1,2-dihydropyridyl, 1,2-dihydroquinolinyl or 1,2,3,4-tetrahydroquinolinyl. The heterocyclic moiety may be attached through any available position including through any available nitrogen atom and it may bear one, two or three substituents including a substituent on any available nitrogen atom.

When Q is a 10-membered bicyclic heterocyclic moiety containing one or two nitrogen atoms it will be appreciated that Q may be attached to $X^1$ from either of the two rings of the bicyclic heterocyclic moiety.

Conveniently Q is, for example, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 2-quinolyl, 3-quinolyl, 5-quinolyl, 6-quinolyl, 7-quinolyl, 1-isoquinolyl, 3-isoquinolyl, 6-isoquinolyl, 7-isoquinolyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalazinyl, 6-phthalazinyl, 1,5-naphthyridin-2-yl, 1,5-naphthyridin-3-yl, 1,6-naphthyridin-3-yl, 1,6-naphthyridin-7-yl, 1,7-naphthyridin-3-yl, 1,7-naphthyridin-6-yl, 1,8-naphthyridin-3-yl, 2,6-naphthyridin-3-yl or 2,7-naphthyridin-3-yl, or hydrogenated derivatives thereof.

Suitable values for substituents which may be present on Q or Ar include, for example:

for halogeno: fluoro, chloro, bromo and iodo;
for (1–4C)alkyl: methyl, ethyl, propyl, isopropyl, butyl, isobutyl and sec-butyl;
for (1–4C)alkoxy: methoxy, ethoxy, propoxy, isopropoxy, and butoxy;
for fluoro-(1–4C)alkyl: fluoromethyl, difluoromethyl, trifluoromethyl, 2-fluoroethyl, 2,2,2-trifluoroethyl and pentafluoroethyl;
for (1–4C)alkylamino: methylamino, ethylamino, propylamino and butylamino; and
for di-[(1–4C)alkyl]amino: dimethylamino, diethylamino and dipropylamino.

Suitable values for substituents which may be present on Q include, for example:

for hydroxy-(1–4C)alkyl: hydroxymethyl, 1-hydroxyethyl, 2-hydroxyethyl, 2-hydroxypropyl and 3-hydroxypropyl;
for amino-(1–4C)alkyl: aminomethyl, 1-aminoethyl, 2-aminoethyl, 2-aminopropyl and 3-aminopropyl;
for (1–4C)alkylamino-(1–4C)alkyl: methylaminomethyl, 2-methylaminoethyl, 3-methylaminopropyl, ethylaminomethyl and 2-ethylaminoethyl;
for di-[1–4C)alkyl]amino(1–4C)alkyl: dimethylaminomethyl, 2-dimethylaminoethyl, 3-dimethylaminopropyl, diethylaminomethyl and 2-diethylaminoethyl;
for amino-(2–4C)alkoxy: 2-aminoethoxy, 3-aminopropoxy and 4-aminobutoxy;
for (1–4C)alkylamino(2–4C)alkoxy: 2-methylaminoethoxy, 3-methylaminopropoxy and 2-ethylaminoethoxy; and
for di-[(1–4C)alkyl]amino(2–4C)alkoxy: 2-dimethylaminoethoxy, 3-dimethylaminopropoxy and 2-diethylaminoethoxy.

A suitable value for Ar when it is phenylene is, for example, 1,3-phenylene or 1,4-phenylene.

A suitable value for Ar when it is a 6-membered heterocyclene moiety containing up to three nitrogen atoms is, for example, pyridylene, pyrimidinylene, pyridazinylene, pyrazinylene or 1,3,5-triazinylene. Conveniently Ar when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

A suitable value for a (2–4C)alkanoylamino substituent which may be present on Ar is, for example, acetamido, propionamido or butyramido.

A suitable value for $R^1$ when it is (1–6C)alkenyl is, for example, methyl, ethyl, propyl, butyl, pentyl or hexyl.

A suitable value for $R^1$ when it is (3–6C)alkenyl is, for example, allyl, 2-butenyl or 3-butenyl; and when it is (3–6C)alkynyl is, for example, 2-propynyl or 2-butynyl.

When $R^2$ and $R^3$ together form a group of the formula $-A^2-X^2-A^3-$ which, together with the carbon atom to which $A^2$ and $A^3$ are attached, defines a ring having 4 to 7 ring atoms then a suitable value for $A^2$ or $A^3$, which may be the same or different, when each is (1–4C)alkylene is, for example, methylene, ethylene, trimethylene or tetramethylene.

Suitable values for the substituents which may be present on said 4- to 7-membered ring include for example:

for halogeno: fluoro, chloro and bromo;
for (1–4C)alkyl: methyl, ethyl, propyl, isopropyl, butyl and isobutyl;
for (1–4C)alkoxy: methoxy, ethoxy, propoxy, isopropoxy and butoxy;
for fluoro-(1–4C)alkyl: fluoromethyl, difluoromethyl, trifluoromethyl, 2-fluoroethyl, 2,2,2-trifluoroethyl and pentafluoroethyl.

A suitable pharmaceutically-acceptable salt of a heterocyclic derivative of the invention is, for example, an acid-addition salt of a heterocyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a heterocyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, heterocyclic derivatives of the formula I wherein:

(a) Q is 2-pyridyl, 3-pyridyl, 3-pyridazinyl, 2-pyrimidinyl or 2-pyrazinyl which may optionally bear one substituent selected from chloro, hydroxy, cyano, methyl, methoxy and trifluoromethyl; and $X^1$, Ar, $R^1$, $R^2$ and $R^3$ have any of the meanings defined hereinbefore;

(b) Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridin-3-yl or 2,7-naphthyridin-3-yl which may optionally bear one, two or three substituents selected from fluoro, chloro, hydroxy, oxo, cyano, methyl, ethyl, propyl, methoxy, trifluoromethyl, 2-fluoroethyl, 2,2,2-trifluoroethyl, 2-aminoethyl, 2-methylaminoethyl and 2-dimethylaminoethyl; and $X^1$, Ar, $R^1$, $R^2$ and $R^3$ have any of the meanings defined hereinbefore;

(c) Q is 1,2-dihydro-2-oxoquinolin-3-yl, 1,2-dihydro-2-oxoquinolin-6-yl, 1,2-dihydro-2-oxoquinolin-7-yl, 3,4-dihydro-4-oxoquinazolin-6-yl, 1,2-dihydro-2-oxo-1,7-naphthyridin-3-yl or 1,2-dihydro-2-oxo-1,8-naphthyridin-3-yl which may optionally bear one or two substituents selected from fluoro, chloro, cyano, methyl, ethyl, methoxy, trifluoromethyl, 2-fluoroethyl and 2-dimethylaminoethyl; and $X^1$, Ar, $R^1$, $R^2$ and $R^3$ have any of the meanings defined hereinbefore;

(d) Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which may optionally bear one or two substituents selected from fluoro, chloro, methyl, ethyl, propyl, trifluoromethyl, 2-fluoroethyl, 2,2,2-trifluorethyl and 2-dimethylaminoethyl; and $X^1$, Ar, $R^1$, $R^2$ and $R^3$ have any of the meanings defined hereinbefore;

(e) Q is 1,2-dihydro-2-oxoquinolin-3-yl, 1,2-dihydro-2-oxoquinolin-5-yl, 1,2-dihydro-2-oxoquinolin-6-yl or 1,2-dihydro-2-oxoquinolin-7-yl which bears a 1-substituent selected from methyl, ethyl, propyl, 2-fluoroethyl and 2,2,2-trifluoroethyl; and which may optionally bear a substituent selected from fluoro, chloro and trifluoromethyl; and $X^1$, Ar, $R^1$, $R^2$ and $R^3$ have any of the meanings defined hereinbefore;

(f) Q is 1,2-dihydro-2-oxoquinolin-6-yl or 1,2-dihydro-2-oxoquinoxalin-6-yl which bears a 1-substituent selected from methyl, ethyl, propyl and 2,2,2-trifluoroethyl, and which may optionally bear a substituent selected from fluoro, chloro, methyl and trifluoromethyl; and $X^1$, Ar, $R^1$, $R^2$ and $R^3$ have any of the meanings defined hereinbefore;

(g) $X^1$ is thio, sulphinyl or sulphonyl; and Q, Ar, $R^1$, $R^2$ and $R^3$ have any of the meanings defined hereinbefore;

(h) Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; and Q, $X^1$, $R^1$, $R^2$ and $R^3$ have any of the meanings defined hereinbefore;

(i) Ar is 1,3-phenylene or 1,4-phenylene which may optionally bear one or two substituents selected from fluoro, chloro, bromo, hydroxy, amino, nitro, methyl, methoxy and trifluoromethyl; and Q, $X^1$, $R^1$, $R^2$ and $R^3$ have any of the meanings defined hereinbefore;

(j) Ar is 2,4-, 2,5-, 3,5- or 2,6-pyridylene or 4,6-pyrimidylene which may optionally bear one substituent selected from chloro, methyl and methoxy; and Q, $X^1$, $R^1$, $R^2$ and $R^3$ have any of the meanings defined hereinbefore;

(k) $R^1$ is methyl, ethyl, allyl or 2-propynyl; and Q, $X^1$, Ar, $R^2$ and $R^3$ have any of the meanings defined hereinbefore;

(l) $R^2$ and $R^3$ together from a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene, ethylene, trimethylene or tetramethylene and $X^2$ is oxy, thio, sulphinyl or sulphonyl, and which ring may bear one or two substituents selected from fluoro, hydroxy, methyl, ethyl, propyl, methoxy, ethoxy and trifluoromethyl; and Q, $X^1$, Ar and $R^1$ have any of the meanings defined hereinbefore; or (m) $R^2$ and $R^3$ together form a group of the formula —$A^2$—$X^2$—$A^3$— which, together with the carbon atom to which $A^2$ and $A^3$ are attached defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl and methoxy; and Q, $X^1$, Ar and $R^1$ have any of the meanings defined hereinbefore;
or a pharmaceutically-acceptable salt thereof.

A preferred compound of the invention comprises a heterocyclic derivative of the formula I wherein Q is 2-quinolyl, 3-quinolyl, 6-quinolyl, 7-quinolyl, 3-isoquinolyl, 6-isoquinolyl, 7-isoquinolyl, 3-cinnolyl, 2-quinazolinyl, 6-quinazolinyl, 2-quinoxalinyl, 6-quinoxalinyl, 6-phthalazinyl, 1,7-naphthyridin-3-yl, 1,7-naphthyridin-6-yl, 1,8-naphthyridin-3-yl or 2,7-naphthyridin-3-yl which may optionally bear one, two or three substituents selected from fluoro, chloro, hydroxy, oxo, cyano, methyl, ethyl, propyl, methoxy, trifluoromethyl, 2-fluoroethyl, 2,2,2-trifluoroethyl, 2-aminoethyl, 2-methylaminoethyl and 2-dimethylaminoethyl: $X^1$ is oxy, thio, sulphinyl, sulphonyl or imino; Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; $R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene, ethylene, trimethylene or tetramethylene and $X^2$ is oxy, thio, sulphinyl or sulphonyl, and which ring may bear one or two substituents selected from fluoro, hydroxy, methyl, ethyl, propyl, methoxy, ethoxy and trifluoromethyl; or a pharmaceutically-acceptable salt thereof.

A further preferred compound of the invention comprises a heterocyclic derivative of the formula I wherein Q is 2-quinolyl, 3-quinolyl, 6-quinolyl, 1,2-dihydro-2-oxoquinolin-3-yl, 1,2-dihydro-2-oxoquinolin-6-yl, 3-isoquinolyl, 2-quinazolinyl, 6-quinazolinyl or 6-quinoxalinyl which may optionally bear one or two substituents selected from fluoro, chloro, methyl, ethyl, trifluoromethyl, 2-fluoroethyl and 2-dimethylaminoethyl; $X^1$ is thio, sulphinyl or sulphonyl; Ar is 1,3-phenylene or 1,4-phenylene which may optionally bear one or two substituents selected from fluoro, hydroxy, amino, nitro, ureido, methoxy, dimethylamino, trifluoromethyl and acetamido; or Ar is 3,5-pyridylene; $R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 5 ring atoms, wherein $A^2$ is ethylene, $A^3$ is methylene or ethylene, and $X^2$ is oxy or thio, and which ring may bear one or two substituents selected from fluoro, methyl, ethyl, propyl, methoxy and trifluoromethyl; or a pharmaceutically-acceptable salt thereof.

A further preferred compound of the invention comprises a heterocyclic derivative of the formula I wherein Q is 1,2-dihydro-2-oxoquinolin-3-yl or 1,2-dihydro-2-oxoquinolin-6-yl or and the corresponding 1-methyl, 1-ethyl, 1-(2-fluoroethyl) and 1-(2,2,2-trifluoroethyl) derivatives; $X^1$ is thio, sulphinyl or sulphonyl; Ar is 1,3-phenylene which may optionally bear one or two substituents selected from fluoro, bromo, methoxy and trifluoromethyl; $R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl, ethyl, propyl and methoxy; or a pharmaceutically-acceptable salt thereof.

A further preferred compound of the invention comprises a heterocyclic derivative of the formula I wherein Q is 1,2-dihydro-2-oxoquinolin-6-yl or 1,2-dihydro-2-oxoquinoxalin-6-yl which may optionally bear one or two substituents selected from fluoro, methyl, ethyl and 2,2,2-trifluoroethyl; $X^1$ is thio, sulphinyl or sulphonyl; Ar is 1,3-phenylene which may optionally bear one fluoro substituent; $R^1$ is methyl; and $R^2$ and $R^3$ together form a group of the formula $-A^2-X^2-A^3-$ which together with the carbon atom to which $A^2$ and $A^3$ are attached, defines a ring having 6 ring atoms, wherein $A^2$ is ethylene, $A^3$ is ethylene and $X^2$ is oxy, and which ring may bear a methyl substituent; or a pharmaceutically-acceptable salt thereof.

An especially preferred compound of the invention comprises a heterocyclic derivative of the formula I wherein Q is 1,2-dihydro-1-methyl-2-oxoquinolin-3-yl, 1,2-dihydro-1-methyl-2-oxoquinolin-6-yl or 1,2-dihydro-1-ethyl-2-oxoquinolin-6-yl; $X^1$ is thio; Ar is 1,3-phenylene, 5-fluoro-1,3-phenylene or 5-trifluoromethyl-1,3-phenylene; $R^1$ is methyl, ethyl or allyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy and which ring may bear a methyl or ethyl substituent alpha to $X^2$; or a pharmaceutically-acceptable salt thereof.

A further especially preferred compound of the invention comprises a heterocyclic derivative of the formula I wherein Q is 1,2-dihydro-1-methyl-2-oxoquinolin-6-yl or 1,2-dihydro-1-ethyl-2-oxoquinolin-6-yl; $X^1$ is thio, sulphinyl or sulphonyl; Ar is 1,3-phenylene, 5-fluoro-1,3-phenylene or 5-trifluoromethyl-1,3-phenylene; $R^1$ is methyl, ethyl or allyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy and which ring may bear a methyl or ethyl substituent alpha to $X^2$; or a pharmaceutically-acceptable salt thereof.

Specific especially preferred compounds of the invention include, for example, the following heterocyclic derivatives of the formula I, or pharmaceutically-acceptable salts thereof: 4-[3-(1,2-dihydro-1-methyl-2-oxoquinolin-6-ylthio)phenyl]-4-methoxytetrahydropyran, 4-[3-(1,2-dihydro-1-ethyl-2-oxoquinolin-6-ylthio)phenyl]-4-methoxytetrahydropyran, 4-[3-(1,2-dihydro-1-methyl-2-oxoquinolin-6-ylthio)-5-fluorophenyl]-4-methoxytetrahydropyran, (2RS,4SR)-4-[3-(1,2-dihydro-1-methyl-2-oxoquinolin-6-ylthio)-5-fluorophenyl]-4-methoxy-2-methyltetrahydropyran, (2S,4R)-4-[3-(1,2-dihydro-1-methyl-2-oxoquinolin-6-ylthio)phenyl]-4-methoxy-2-methyltetrahydropyran, (2S,4R)-4-[3-(1,2-dihydro-1-methyl-2-oxoquinolin-6-ylsulphonyl)phenyl]-4-methoxy-2-methyltetrahydropyran and (2RS,4SR)-[3-(1,2-dihydro-1-methyl-2-oxoquinolin-6-ylsulphonyl)-5-fluorophenyl]-4-methoxy-2-methyltetrahydropyran.

Further especially preferred compounds of the invention include, for example, the following heterocyclic derivatives of the formula I, or pharmaceutically-acceptable salts thereof: 4-[3-(8-fluoro-1,2-dihydro-1-methyl-2-oxoquinolin-6-ylthio)phenyl]-4-methoxytetrahydropyran and 4-[3-(1,2-dihydro-1,8-dimethyl-2-oxoquinolin-6-ylthio)phenyl]-4-methoxytetrahydropyran.

A compound of the invention comprising a heterocyclic derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Q, $X^1$, Ar, $R^1$, $R^2$ and $R^3$ have any of the meanings defined hereinbefore.

(a) The coupling, in the presence of a suitable base, of a compound of the formula Q-$X^1$-H with a compound of the formula II wherein Z is a displaceable group; provided that, when there is and amino, imino, alkylamino or hydroxy group in Q, Ar, $R^1$, $R^2$ or $R^3$, any amino, imino, alkylamino or hydroxy group may be protected by a conventional protecting group or alternatively any such group need not be protected; whereafter any undesired protecting group in Q, Ar, $R^1$, $R^2$ or $R^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the coupling reaction is, for example, an alkali or alkaline earth metal carbonate, (1-4C-)alkoxide, hydroxide or hydride, for example sodium carbonate, potassium carbonate, sodium ethoxide, sodium butoxide, sodium hydroxide, potassium hydroxide, sodium hydride or potassium hydride. The coupling reaction is conveniently performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently in the range 70° to 150° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino, imino or alkylamino group is, for example, an acyl group for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula Q—$X^1$—H and of the formula II may be obtained by standard procedures of organic chemistry. Thus, for example, when a starting material of the formula Q—SH is required, it may be obtained by, for example, the reaction of a heterocyclic moiety of the formula Q—H wherein Q has any of the meanings defined hereinbefore with a halosulphonylating agent such as, for example, chlorosulphonic acid, in a suitable solvent or diluent, for example dichloroethane or pyridine, and at a temperature in the range, for example 40° to 150° C., conveniently at or near 100° C. The intermediate of, for example, the formula $Q-SO_2-Cl$ so produced may be reduced to a compound of the formula Q-SH by a conventional reducing agent such as, for example, a suitable reducing metallic salt such as Aa metallic halide, for example a stannous halide, conveniently stannous chloride, in a suitable solvent or diluent such as a (2–4C)alkanoic acid, for example acetic acid, and at a temperature in the range, for example, 40° to 150° C., conveniently in the range 80° to 100° C. Alternatively the reducing agent may be a suitable reducing metal, such as zinc or iron, in the presence of a strong acid, such as hydrochloric, sulphuric or phosphoric acid, and at a temperature in the range, for example 10° to 150° C., conveniently at or near 100° C.

Conveniently intermediates of the formula II wherein Z, Ar, $R^1$, $R^2$ and $R^3$ have the meanings defined hereinbefore, may be obtained by way of compounds of the formula Z—Ar—Y, wherein Z and Ar have the meanings defined hereinbefore and Y is, for example, a halogeno, formyl, alkanoyl, nitrile or alkoxycarbonyl group, as illustrated in accompanying Scheme I (set out hereinafter). Thus, for example, in the accompanying non-limiting Examples it is shown how to convert a compound of the formula Z—Ar—Y wherein Y is a halogeno group to a compound of the formula II.

It will also be appreciated that the intermediate of the formula II may conveniently be obtained from the compound of the formula Z—Ar—Y, as defined hereinbefore, by reversing the order of introduction of the groups $R^2$ and $R^3$ which is used in Scheme I.

(b) The coupling, in the presence of a suitable base as defined hereinbefore, of a compound of the formula III with a compound of the formula Q—Z wherein Z is a displaceable group as defined hereinbefore; provided that, when there is an amino, imino, alkylamino or hydroxy group in Q, Ar, $R^1$, $R^2$ or $R^3$, any amino, imino, alkylamino or hydroxy group may be protected by a conventional protecting group as defined hereinbefore or alternatively any such group need not be protected; whereafter any desired protecting group in Q, Ar, $R^1$, $R^2$ or $R^3$ is removed by conventional means.

The coupling reaction is conveniently performed in a suitable inert solvent as defined hereinbefore and at a temperature in the range, for example, 10° to 200° C., conveniently in the range 70° to 150° C. The reaction may conveniently be performed in the presence of a suitable catalyst as defined hereinbefore.

The starting materials of the formula Q—Z and of the formula III may be obtained by standard procedures of organic chemistry. The preparation of such starting materials is described within the accompanying non-limiting Examples which are provided for the purpose of illustration only. Alternatively necessary starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group defined hereinbefore. Examples of such groups are given in Scheme II. The conditions for the introduction and removal of such protecting groups are described in standard textbooks of organic chemistry such as, for example, "Protective Groups in Organic Synthesis" by T W Green (J Wiley and Sons, 1981).

In particular a suitable protecting group for a mercapto group is, for example, an acyl group, for example a (2–4C)alkanoyl group (especially acetyl), a (1–4C)alkoxycarbonyl group (especially tert-butoxycarbonyl) or an aroyl group (especially benzoyl). The deprotection conditions for the above protecting groups necessarily vary with the choice of protecting group. Thus, for example, an acyl group such as alkanoyl or alkoxycarbonyl or an aroyl group may be removed by, for example, hydrolysis with a suitable base such as an alkali metal hydroxide, for example lithium or sodium hydroxide. Alternatively an acyl group such as tert-butoxycarbonyl group may be removed, for example, by treatment with a suitable acid such as hydrochloric, sulphuric or trifluoroacetic acid.

(c) The alkylation, in the presence of a suitable base as defined hereinbefore, of a compound of the formula IV with a compound of the formula $R^1$—Z, wherein $R^1$ and Z have the meanings defined hereinbefore, provided that, when there is an amino, imino, alkylamino or hydroxy group in Q, Ar, $R^1$, $R^2$ or $R^3$ any amino, imino, alkylamino or hydroxy group may be protected by a conventional protecting group or alternatively any such group need not be protected; whereafter any undesired protecting group in Q, Ar, $R^1$, $R^2$ or $R^3$ is removed by conventional means.

The tertiary alcohol starting material of the formula IV may be obtained by standard procedures of organic chemistry. Conveniently, and as illustrated in accompanying Scheme III (set out hereinafter), intermediates of the formulae Q—$X^1$—Ar—Y, wherein Q, $X^1$ and Ar have the meanings defined hereinbefore and Y is, for example, a halogeno, formyl, alkanoyl, nitrile or alkoxycarbonyl group may be utilised in the preparation of the tertiary alcohol starting material of the formula IV.

(d) For the production of those compounds of the formula I wherein $X^1$ is a sulphinyl or sulphonyl group; or wherein $R^2$ and $R^3$ together form a group of the formula —$A^2$—$X^2$—$A^3$— and $X^2$ is a sulphinyl or sulphonyl group; the oxidation of a compound of the formula I wherein $X^1$ is a thio group; or wherein $R^2$ and $R^3$ together form a group of the formula —$A^2$—$X^2$—$A^3$— and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein Ar bears an alkanoylamino substituent, the acylation of a compound of the formula I wherein Ar bears an amino substituent.

A suitable acylating agent is, for example, any agent known in the art for the acylation of amino to acylamino, for example an acyl halide, for example a (2–6-C)alkanoyl chloride or bromide, in the presence of a suitable base, an alkanoic acid anhydride, for example a (2–6C)alkanoic acid anhydride, or an alkanoic acid mixed anhydride, for example the mixed anhydride formed by the reaction of an alkanoic acid and a (1–4C-)alkoxycarbonyl halide, for example a (1–4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein Q bears an alkyl or substituted alkyl substituent on an available nitrogen atom, or wherein Ar bears an alkoxy substituent, the alkylation of a compound of the formula I wherein Q bears a hydrogen atom on said available nitrogen atom, or wherein Ar bears a hydroxy substituent.

A suitable alkylating agent is, for example, any agent known in the art for the alkylation of an available nitrogen atom, or of hydroxy to alkoxy, for example an alkyl or substituted alkyl halide, for example a (1–6C)alkyl chloride, bromide or iodide or a substituted (1–4C)alkyl chloride, bromide or iodide, in the presence of a suitable base as defined hereinbefore. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently at or near ambient temperature.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the heterocyclic derivatives of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(T \times B_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $T \times B_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure $LTC_4$ and $PGE_2$. This test provides an indication of inhibitory effects against 5-LO and cyclooxygenase in a nonproteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a β-adrenergic blocking agent (propranolol) and a cyclooxygenase inhibitor (indomethacin), using the procedure of W. H. Anderson et alia (*British J Pharmacology*, 1983, 78(1), 67-574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days). At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01–30 $\mu M$;

Test b):

$IC_{50}$ ($LTB_4$) in the range, for example, 0.01–40 $\mu M$ $IC_{50}$ ($TxB_2$) in the range, for example 40–200 $\mu M$;

Test c): oral $ED_{50}$ ($LTB_4$) in the range, for example, 0.5–100 mg/kg;

Test d):

$IC_{50}$ ($LTC_4$) in the range, for example, 0.001–1 $\mu M$, $IC_{50}$ ($PGE_2$) in the range, for example, 20–1000 $\mu M$;

Test e): inhibition of inflammation in the range, for example, 0.3–100 $\mu g$ intradermally;

Test f): $ED_{50}$ in the range, for example, 0.5–10 mg/kd i.v.;

Test g): oral $ED_{50}$($LTB_4$) in the range, for example, 0.5–50 mg/kg.

No overt toxicity or other untoward effects are present in tests c), e), f) and/or g) when compounds of the formula I are administered at several multiples of their minimum inhibitory dose or concentration.

Thus, by way of example, the compound 4-[3-(1,2-dihydro-1-methyl-2-oxoquinolin-6-ylthio)phenyl]-4-methoxytetrahydropyran has an $IC_{50}$ of <0.04 $\mu M$ against $LTB_4$ in test b), an oral $ED_{50}$ of 1.5 mg/kg versus $LTB_4$ in test c), and an oral $ED_{50}$ of 1 mg/kg versus $LTB_4$ in test g). In general those compounds of the formula I which are particularly preferred have an $IC_{50}$ of >1 $\mu M$ against $LTB_4$ in test b), and an oral $ED_{50}$ of <100 mg/kg against $LTB_4$ in tests c) and g).

These compounds are examples of heterocyclic derivatives of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a heterocyclic derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a heterocyclic derivative of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a heterocyclic derivative of the formula I will naturally vary according to the nature and severity of the conditions, the age and sex of the animal or patient and the route of administration, according to well known principles of medicine. As mentioned above, heterocyclic derivatives of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a heterocyclic derivative of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°-25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were generally determined after recrystallisation from a conventional organic solvent such as ethanol, methanol, acetone, ether or hexane, alone or in admixture; and (viii) the following abbreviations have been used:

THF tetrahydrofuran;
DMF N,N-dimethylformamide.

EXAMPLE 1

A mixture of 1,2-dihydro-6-iodo-1-methylquinolin-2-one (0.45 g), 4-(3-mercaptophenyl)-4-methoxytetrahydropyran (0.45 g), cuprous chloride (0.05 g), potassium carbonate (0.4 g) and DMF (0.5 ml) was heated to reflux under an atmosphere of argon for 1 hour. The mixture was cooled to ambient temperature and partitioned between diethyl ether and water. The organic phase was washed with water, dried ($MgSO_4$) and evaporated. The residue was purified by column chromatography using increasingly polar mixtures of hexane and ethyl acetate as eluent. There was thus obtained 4-[3-(1,2-dihydro-1-methyl-2-oxoquinolin-6-ylthio)-phenyl]-4-methoxytetrahydropyran (0.13 g, 22%), m.p. 113°-116° C.

NMR Spectrum ($CDCl_3$, δ values) 1.95(m, 4H), 2.95(s, 3H), 3.7(s, 3H), 3.8(m, 4H), 6.7(d, 1H), 7.2-7.6(m, 8H).

The 1,2-dihydro-6-iodo-1-methylquinolin-2-one used as a starting material was obtained as follows:

Sodium hydride (60% w/w dispersion in mineral oil; 0.84 g) was added in portions to a mixture of 2-hydroxyquinoline (2.9 g) and DMF (15 ml) and the mixture was stirred at ambient temperature for 1 hour. Methyl iodide (5.7 g) was added and the mixture was stirred at ambient temperature for 30 minutes. The mixture was partitioned between diethyl ether and brine. The organic phase was washed with brine, dried ($MgSO_4$) and evaporated. The residue was purified by column chromatography using increasingly polar mixtures of ethyl acetate and hexane as eluent. There was thus obtained 1,2-dihydro-1-methylquinolin-2-one (2.5 g), m.p. 71°-73° C.

A mixture of a portion (1 g) of the product so obtained, iodine monochloride (2.3 g) and glacial acetic acid (10 ml) was heated to 80° C. for 1.5 hours. The mixture was poured into water (10 ml) and sodium sulphite (approx. 5 g) was added to destroy the excess of iodine monochloride. The mixture was extracted with chloroform (2×20 ml) and the combined extracts were dried ($MgSO_4$) and evaporated. The residue was purified by column chromatography on reversed-phase silica using decreasingly polar mixtures of water and methanol as eluent. There was thus obtained 1,2-dihydro-6-iodo-1-methylquinolin-2-one (0.48 g), as an oil.

NMR Spectrum ($CDCl_3$, δ values) 3.67(s, 3H), 6.7(d, 1H), 7.1(d, 1H), 7.55(d, 1H), 7.8(q, 1H), 7.87(d, 1H).

The 4-(3-mercaptophenyl)-4-methoxytetrahydropyran used as a starting material was obtained as follows:

A solution of 1,3-dibromobenzene (23.8 g) in THF (120 ml) was cooled to −78° C. under an atmosphere of argon and n-butyl lithium (1.6M in hexane, 62.5 ml) was added dropwise. The mixture was stirred at −78° C. for 30 minutes and a solution of tetrahydropyran-4-one (10 g) in THF (40 ml) was added. The resultant suspension was stirred at −78° C. for 1 hour, allowed to warm to ambient temperature and then stirred for 30 minutes. The mixture was poured into brine (250 ml) and extracted with diethyl ether. The organic phase was dried ($MgSO_4$) and evaporated. The residue was triturated under hexane and the resultant solid (16.8 g) was filtered off.

A solution of the product so obtained in DMF (100 ml) was added dropwise to a slurry of sodium hydride (60% w/w dispersion in mineral oil; 5.25 g) in DMF (10 ml) and the mixture was stirred at ambient temperature for 90 minutes. Methyl iodide (36.5 g) was added and the mixture was stirred at ambient temperature for 16 hours. Ethanol (2 ml) and water (500 ml) were added in turn and the mixture was extracted with diethyl ether (3×200 ml). The combined extracts were washed with water, dried (MgSO$_4$) and evaporated. The residue was purified by column chromatography using increasingly polar mixtures of hexane and ethyl acetate as eluent. There was thus obtained 4-(3-bromophenyl)-4-methoxytetrahydropyran (12 g, 44%) as a solid.

NMR Spectrum (CDCl$_3$, δ values) 1.88–2.1(m, 4H), 3.0(s, 3H), 3.78–3.95(m, 4H), 7.2–7.35(m, 2H), 7.42(m, 1H), 7.55(m, 1H).

A solution of a portion (1 g) of the product so obtained in THF (4 ml) was cooled to −80° C. under an atmosphere of argon and n-butyl lithium (1.6M in hexane, 2.4 ml) was added dropwise. The mixture was stirred at −80° C. for 30 minutes, sulphur (0.12 g) was added and the mixture was stirred at −80° C. for a further 30 minutes. Water (10 ml) was added and the mixture was allowed to warm to ambient temperature. The mixture was extracted with diethyl ether (10 ml). The aqueous phase was acidified to pH4 by the addition of dilute aqueous hydrochloric acid solution and extracted with diethyl ether (2×10 ml). The combined organic extracts were dried (MgSO$_4$) and evaporated. There was thus obtained the required starting material as an oil (0.5 g) which crystallised on standing and was used without further purification.

EXAMPLE 2

Using a similar procedure to that described in Example 1, except that 1,2-dihydro-6-iodo-1-ethylquinolin-2-one was used in place of the corresponding 1-methylquinolin-2-one, there was obtained 4-[3-(1,2-dihydro-1-ethyl-2-oxoquinolin-6-ylthio)phenyl]-4-methoxytetrahydropyran, as a gum in 65% yield.

NMR Spectrum (CDCl$_3$, δ values) 1.35(t, 3H), 1.95(m, 4H), 2.96 (s, 3H), 3.7(m, 4H), 4.35(q, 2H), 6.7(d, 1H), 7.1–7.6(m, 8H).

The 1,2-dihydro-6-iodo-1-ethylquinolin-2-one used as a starting material was obtained using a similar procedure to that described in the portion of Example 1 which is concerned with the preparation of the starting material 1,2-dihydro-6-iodo-1-methylquinolin-2-one, except that ethyl iodide was used in place in methyl iodide. There were thus obtained in turn 1,2-dihydro-1-ethylquinolin-2-one, m.p. 52°–54° C., and the required starting material as an oil.

NMR Spectrum (CDCl$_3$, δ values), 1.35(t, 3H), 4.35(q, 2H), 6.7(d, 1H), 7.13(d, 1H), 7.55(d, 1H), 7.8(q, 1H), 7.88(d, 1H).

EXAMPLE 3

Using a similar procedure to that described in Example 1, except that 1,2-dihydro-6-iodo-1-(2,2,2-trifluoroethyl)quinolin-2-one was used in place of 1,2-dihydro-6-iodo-1-methylquinolin-2-one, there was obtained 4-[3-(1,2-dihydro-2-oxo-1-(2,2,2-trifluoroethyl)quinolin-6-ylthio)phenyl]-4-methoxytetrahydropyran in 25% yield, m.p. 138°–140° C.

NMR Spectrum (CDCl$_3$, δ values) 1.8–2.1(m, 4H), 2.95(s, 3H), 3.7–3.9(m, 4H), 5.0(q, 2H), 6.7(d, 1H), 7.2–7.7(m, 8H).

The 1,2-dihydro-6-iodo-1-(2,2,2-trifluoroethyl)quinolin-2-one used as a starting material was obtained as follows:

Sodium hydride (60% w/w dispersion in mineral oil; 1.45 g) was added in portions to a mixture of 2-hydroxyquinoline (5 g) and DMF (25 ml) and the mixture was stirred at ambient temperature for 30 minutes. 2,2,2-Trifluoroethyl tosylate (10 g) was added and the mixture was heated to 140° C. for 8 hours. The mixture was cooled to ambient temperature and partitioned between diethyl ether and water. The organic phase was washed with water, dried (MgSO$_4$) and evaporated. The residue was purified by column chromatography using increasingly polar mixtures of hexane and ethyl acetate as eluent. There was thus obtained 1,2-dihydro-1-(2,2,2-trifluoroethyl)quinolin-2-one as an oil (2.8 g).

A mixture of the material so obtained, iodine monochloride (4 g) and glacial acetic acid (25 ml) was heated to 60° C. for 7 hours. The mixture was poured into water (50 ml) and sodium sulphite (approx. 10 g) was added to destroy the excess of iodine monochloride. The mixture was extracted with diethyl ether (2×50 ml) and the combined extracts were washed with water, dried (MgSO$_4$) and evaporated. The residue was purified by column chromatography on reversed-phase silica using decreasingly polar mixtures of water and methanol as eluent. The solid so obtained was recrystallised from a mixture of hexane and ethyl acetate. There was thus obtained the required starting material (0.7 g).

NMR Spectrum (CDCl$_3$, δ values) 5.0(m, 2H), 6.7(d, 1H), 7.1(d, 1H), 7.6(d, 1H), 7.85(q, 1H), 7.9(d, 1H).

EXAMPLE 4

A mixture of 1,2-dihydro-6-iodo-1-methylquinolin-2-one (0.3 g), 4-(5-fluoro-3-mercaptophenyl)-4-methoxytetrahydropyran (0.37 g), cuprous chloride (0.05 g), potassium carbonate (0.15 g) and DMF (0.5 ml) was heated to 120° C. under an atmosphere of argon for 2 hours. The mixture was cooled to ambient temperature and partitioned between diethyl ether and water. The organic phase was washed with water, dried (MgSO$_4$) and evaporated. The residue was purified by column chromatography using increasingly polar mixtures of hexane and ethyl acetate as eluent. There was thus obtained a gum which was triturated in a 10:1 v/v mixture of hexane and ethyl acetate. There was thus obtained 4-[3-(1,2-dihydro-1-methyl-2-oxoquinolin-6-ylthio)-5-fluorophenyl]-4-methoxytetrahydropyran (0.16 g), m.p. 125°–128° C.

NMR Spectrum (CDCl$_3$, δ values) 1.85–2.05(m, 4H), 2.95(s, 3H), 3.74(s, 3H), 3.76–3.9(m, 4H), 6.75(m, 2H), 6.93(m, 1H), 7.1(m, 1H), 7.38(d, 1H), 7.58–7.7(m, 3H).

The 4-(5-fluoro-3-mercaptophenyl)-4-methoxytetrahydropyran used as a starting material was obtained as follows:

Benzyl mercaptan (0.94 ml) was added dropwise to a mixture of sodium hydride (60% w/w dispersion in mineral oil; 0.35 g) and DMF (5 ml) which was cooled in a water bath. The mixture was stirred at ambient temperature for 30 minutes. The mixture so obtained was added dropwise to a mixture of 1-bromo-3,5-difluorobenzene (2.78 ml) and DMF (5 ml) which was cooled in an ice bath to 5° C. The resultant mixture was stirred at ambient temperature for 1 hour. The mixture was partitioned between diethyl ether and water. The organic phase was washed with water, dried (MgSO$_4$) and evaporated. There was thus obtained benzyl 3-bromo-5-fluorophenyl sulphide (2.5 g).

NMR Spectrum (CDCl$_3$, δ values) 4.13(s, 2H), 6.90(m, 1H), 7.04(m, 1H), 7.2–7.35(m, 6H).

A Grignard reagent was prepared by heating a mixture of 1,2-dibromoethane (10 drops), magnesium (0.24 g) and THF (25 ml) to 60° C. for 5 minutes, by adding benzyl 3-bromo-5-fluorophenyl sulphide (2.5 g) and by heating the resultant mixture to 60° C. for 30 minutes. The reagent was cooled in an ice bath, tetrahydropyran-4-one (0.8 ml) was added and the mixture was stirred for 30 minutes and then allowed to warm to ambient temperature. A saturated aqueous ammonium chloride solution (30 ml) was added and the mixture was partitioned between diethyl ether and water. The organic phase was washed with water and with brine, dried (MgSO$_4$) and evaporated. The residue was purified by column chromatography using initially hexane and then increasingly polar mixtures of hexane and ethyl acetate as eluent. There was thus obtained 4-(3-benzylthio-5-fluorophenyl)-4-hydroxytetrahydropyran (1.02 g).

Sodium hydride (60% w/w dispersion in mineral oil; 0.2 g) was added portionwise to a mixture of the product so obtained and DMF (5 ml) and the mixture was stirred at ambient temperature for 1 hour. Methyl iodide (0.6 ml) was added and the mixture was stirred at ambient temperature for 1 hour. The mixture was partitioned between diethyl ether and water. The organic phase was dried (MgSO$_4$) and evaporated. There was thus obtained 4-(3-benzylthio-5-flrorophenyl)-4-methoxytetrahydropyran (0.8 g) as an oil.

NMR Spectrum (CDCl$_3$, δ values) 1.85(m, 4H), 2.91(s, 3H), 3.78(m, 4H), 4.12(s, 2H), 6.85–7.05(m, 3H), 7.25(m, 5H).

3-Chloroperbenzoic acid (55% w/w technical grade; 0.38 g) was added portionwise to a mixture of a portion (0.4 g) of the product so obtained and chloroform (4 ml) which was cooled in an ice bath to 0° C. The mixture was stirred at 0° C. for 30 minutes and then allowed to warm to ambient temperature. Calcium hydroxide (0.13 g) was added and the mixture was stirred at ambient temperature for 15 minutes. The mixture was filtered and the filtrate was evaporated. Trifluoroacetic anhydride (3 ml) was added to the residue so obtained and the mixture was heated to reflux for 30 minutes. The mixture was evaporated. Methanol (10 ml) and triethylamine (10 ml) were added to the residue and the resultant mixture was evaporated. There was thus obtained 4-(5-fluoro-3-mercaptophenyl)-4-methoxytetrahydropyran (0.37 g) as a gum which was used as the required starting material without further purification.

EXAMPLE 5

Using a similar procedure to that described in Example 4, except that (2RS,4SR)-4-(5-fluoro-3-mercaptophenyl)-4-methoxy-2-methyltetrahydropyran was used in place of 4-(5-fluoro-3-mercaptophenyl)-4-methoxytetrahydropyran, there was obtained (2RS,4SR)-4-[3-(1,2-dihydro-1-methyl-2-oxoquinolin-6-ylthio)-5-fluorophenyl]-4-methoxy-2-methyltetrahydropyran in 40% yield as an oil.

NMR Spectrum (CDCl$_3$, δ values) 1.18(d, 3H), 1.52(q, 1H), 1.9(m, 3H), 2.95(s, 3H), 3.54(s, 3H), 3.80–3.95(m, 3H), 6.75(m, 2H), 6.92(m, 1H), 7.08(m, 1H), 7.38(d, 1H), 7.55–7.72(m, 3H).

The (2RS,4SR)-4-(5-fluoro-3-mercaptophenyl)-4-methoxy-2-methyltetrahydropyran used as a starting material was obtained in 30% yield using similar procedures to those described in the portion of Example 4 which is concerned with the preparation of starting materials, except that 2-methylteterahydropyran-4-one (J. Amer. Chem. Soc., 1982, 104, 4666) was used in place of tetrahydropyran-4-one. The intermediate (2RS,4SR)-4-(3-benzylthio-5-fluorophenyl)-4-methoxy-2-methyltetrahydropyran, i.e. the diastereoisomer having the 2-methyl and 4-methoxy substituents in a trans-relationship, was purified by column chromatography using increasingly polar mixtures of hexane and ethyl acetate as eluent and gave the following NMR data (CDCl$_3$, δ values) 1.2(d, 3H), 1.45(q, 1H), 1.83(m, 3H), 2.92(m, 3H), 3.85(m, 3H), 4.15(s, 2H), 6.85–7.05(m, 3H), 7.28(m, 5H).

EXAMPLE 6

Using a similar procedure to that described in Example 1, except that (2S,4R)-4-(3-mercaptophenyl)-4-methoxy-2-methyltetrahydropyran was used in place of 4-(3-mercaptophenyl)-4-methoxytetrahydropyran, there was obtained (2S,4R)-4-[3-(1,2-dihydro-1-methyl-2-oxoquinolin-6-ylthio)phenyl]-4-methoxy-2-methyltetrahydropyran in 45% yield, m.p. 93°–96° C.

NMR Spectrum (CDCl$_3$, δ values) 1.2(d, 3H), 1.5(q, 1H), 1.8–2.0(m, 3H), 2.95(s, 3H), 3.7(s, 3H), 3.8–4.0(m, 3H), 6.7(d, 1H), 7.1–7.6(m, 8H).

The (2S,4R)-4-(3-mercaptophenyl-4-methoxy-2-methyltetrahydropyran used as a starting material was obtained as follows:

A Grignard reagent was prepared by heating a mixture of 3-bromoiodobenzene (4.35 g), magnesium (0.32 g) and diethyl ether (35 ml) to reflux for 30 minutes. The mixture was cooled in an ice/water bath to 5° C. and a solution of (2S)-2-methyltetrahydropyran-4-one (1 g) in diethyl ether (5 ml) was added dropwise. The mixture was stirred and allowed to warm to ambient temperature over 1 hour. A saturated aqueous ammonium chloride solution (30 ml) was added and the mixture was extracted with diethyl ether (2×50 ml). The combined extracts were washed with brine, dried (MgSO$_4$) and evaporated.

Sodium hydride (60% w/w dispersion in mineral oil; 0.29 g) was added to a solution of the residue so obtained in DMF (6 ml) and the mixture was stirred at ambient temperature for 2 hours. Methyl iodide (2.6 g) was added and the mixture was stirred at ambient temperature for 18 hours. The mixture was partitioned between diethyl ether and water. The organic layer was washed with water, dried (MgSO$_4$) and evaporated. The residue was purified by column chromatography using increasingly polar mixture of hexane and ethyl acetate as eluent. There was thus obtained (2S,4R)-4-(3-bromophenyl)-4-methoxy-2-methyltetrahydropyran (1 g) as an oil.

NMR Spectrum (CDCl$_3$, δ values) 1.2(d, 3H), 1.55(q, 1H), 1.95(m, 3H), 3.0(s, 3H), 3.8–4.1(m, 3H), 7.2–7.6(m, 4H).

Using a similar procedure to that described in the last paragraph of the portion of Example 1 which is concerned with the preparation of starting materials, the product so obtained was converted into the required starting material in 45% yield.

The (2S)-2-methyltetrahydropyran-4-one, used as a starting material above, was obtained as follows:

Sodium bis-(2-methyoxyethoxy)aluminium hydride (3.4M in toluene, 200 ml) was added over a period of 30 minutes to a solution of (−)-(2S,3S,4S)-2,3-epoxyhept-6-en-4-ol (29 g; J. Org. Chem., 1983, 48, 5093, compound No. (−)14 therein) in THF (1100 ml) which had been cooled to −15° C. and the mixture was stirred for 16 hours and allowed to warm to ambient temperature. The mixture was cooled in an ice bath and dilute aqueous sulphuric acid (10% w/v, 1350 ml) was added slowly. Sodium chloride was added to produce two phases. The organic phase was separated and the aqueous phase was extracted with ethyl acetate. The combined organic phases were washed with brine, dried (MgSO$_4$) and evaporated. The residue was purified by column chromatography using a 2:3 v/v mixture of hexane and ethyl acetate as eluent. There was thus obtained (2S,4S)-hept-6-ene-2,4-diol (20 g, 67%), as an oil.

NMR Spectrum (CDCl$_3$, δ values) 1.23(d, 3H), 1.63(t, 2H), 2.18-2.4(m, 4H), 3.93-4.38(m, 2H), 5.08-5.25(m, 2H), 5.70-5.96(m, 1H).

A solution of a portion (5.6 g) of the product so obtained in methanol (875 ml) was cooled to −20° C. and a stream of ozone-containing oxygen (approximately 5% ozone) was bubbled into the solution for 130 minutes. Oxygen gas and then argon were bubbled into the solution to remove any excess ozone. Dimethyl sulphide (20 ml) was added and the mixture was allowed to warm to ambient temperature. The mixture was evaporated and the residue was purified by column chromatography using ethyl acetate as eluent. There was thus obtained as a mixture of diastereoisomers (2S,4R,6R)- and (2S,4R,6S)-4,6-dihydroxy-2-methyltetrahydropyran (3.7 g, 67%), as an oil.

After repetition of the above steps, a saturated solution of hydrogen chloride in ethanol (90 drops) was added to a solution of the product so obtained (19 g) in ethanol (90 ml) which had been cooled in an ice bath and the mixture was stored at 5° C. for 16 hours. The mixture was evaporated to give as a mixture of diastereoisomers (2S,4R,6R)- and (2S,4R,6S)-6-ethoxy-4-hydroxy-2-methyltetrahydropyran in quantitative yield, as an oil, which was used without further purification.

A solution of the product so obtained in DMF (45 ml) was cooled to 0° C. and there were added in turn imidazole (20.4 g) and molecular sieve (4 Angstrom, 5 g). Triethylsilyl chloride (24.3 ml) was added dropwise and the mixture was stirred at 0° C. for 2 hours. The mixture was poured onto ice and an ethyl acetate extract was taken. The organic phase was dried (MgSO$_4$) and evaporated. The residue was dissolved in ether (300 ml) and the solution was washed with cold water. The organic layer was separated, dried (MgSO$_4$) and evaporated to give as a mixture of diastereoisomers (2S,4R,6R)- and (2S,4R,6S)-6-ethoxy-2-methyl-4-triethylsilyloxytetrahydropyran (36 g, 91%), which was used without further purification.

Triethylsilane (15.7 g) and trimethylsilyl trifluoromethanesulphonate (29.1 g) were added in turn to a solution of the product so obtained in methylene chloride (300 ml) which had been cooled to 5° C. and the mixture was stirred at 5° C. for 30 minutes. The mixture was poured into ice-cold water (50 ml) and the resultant mixture was stirred for 5 minutes. The mixture was neutralised by the portionwise addition of sodium bicarbonate. The organic layer was separated and the aqueous layer was saturated with sodium chloride and extracted with ethyl acetate. The organic solutions were combined, dried (MgSO$_4$) and evaporated. The residue was purified by column chromatography using a 4:1 v/v mixture of hexane and ethyl acetate as eluent. There was thus obtained (2S,4S)-4-hydroxy-2-methyltetrahydropyran (6.2 g, 41%).

NMR Spectrum (CDCl$_3$, δ values) 1.15-1.25(m, 4H), 1.4-1.6(m, 1H), 1.8-2.0(m, 2H), 3.3-3.5(m, 2H), 3.7-3.8(m, 1H), 4.0(m, 1H).

Jones reagent (*J. Chem. Soc*, 1951, 2407; 13.3 ml of a 8M solution of chromium trioxide in aqueous sulphuric acid) was added dropwise to a solution of the product so obtained in acetone (250 ml) which was cooled to 5° C. Isopropanol (approximately 20 drops) was added to destroy the excess of oxidant and the mixture was stirred at ambient temperature for 30 minutes. The mixture was filtered and the filtrate was evaporated. The residue was dissolved in diethyl ether (10 ml) and the solution was filtered through Kieselgel 60H silica and evaporated. There was thus obtained (2S)-2-methyltetrahydropyran-4-one (4.85 g, 81%), as an oil.

NMR Spectrum (CDCl$_3$, δ values) 1.3(d, 3H), 2.2-2.7(m, 4H), 3.6-3.8(m, 2H), 4.2-4.3(m, 1H).

EXAMPLE 7

A solution of potassium peroxymonosulphate (0.4 g) in water (0.5 ml) was added to a solution of (2S,4R)-4-[3-(1,2-dihydro-1-methyl-2-oxoquinolin-6-ylthio)-phenyl]-4-methoxy-2-methyltetrahydropyran (0.15 g) in ethanol (0.5 ml) and the mixture was stirred at ambient temperature for 48 hours. The mixture was partitioned between methylene chloride and water. The organic layer was washed with water, dried (MgSO$_4$) and evaporated. The residue was recrystallised from a mixture of hexane and diethyl ether. There was thus obtained (2S,4R)-4-[3-(1,2-dihydro-1-methyl-2-oxoquinolin-6-ylsulphonyl)phenyl]-4-methoxy-2-methyltetrahydropyran (0.11 g, 65%), m.p. 156°-159° C.

NMR Spectrum (CDCl$_3$, δ values) 1.2(d, 3H), 1.6(q, 1H), 1.9-2.0(m, 3H), 2.95(s, 3H), 3.7(s, 3H), 3.8-4.0(m, 4H), 6.85(d, 1H), 7.4-8.2(m, 8H).

EXAMPLE 8

Using a similar procedure to that described in Example 7, 4-[3-(1,2-dihydro-1-methyl-2-oxoquinolin-6-ylthio)phenyl]-4-methoxytetrahydropyran was oxidised with potassium peroxymonosulphate to give 4-[3-(1,2-dihydro-1-methyl-2-oxoquinolin-6-ylsulphonyl)-phenyl]-4-methoxytetrahydropyran in 50% yield, m.p. 204°-207° C. (recrystallised from methanol).

NMR Spectrum (CDCl$_3$, δ values) 1.9-2.1(m, 4H), 2.95(s, 3H), 3.7(s, 3H), 3.8-3.9(m, 4H), 6.8(d, 1H), 7.4-8.2(m, 8H).

EXAMPLE 9

Using a similar procedure to that described in Example 7, (2RS,4SR)-4-[3-(1,2-dihydro-1-methyl-2-oxoquinolin-6-ylthio)-5-fluorophenyl]-4-methoxy-2-methyltetrahydropyran was oxidised with potassium peroxymonosulphate to give (2RS,4SR)-4-[3-(1,2-dihydro-1-methyl-2-oxoquinolin-6-ylsulphonyl)-5-fluorophenyl]-4-methoxy-2-methyltetrahydropyran in 70% yield, m.p. 85°-88° C.

NMR Spectrum (CDCl$_3$, δ values) 1.2(d, 3H), 1.55(q, 1H), 1.85-2.02(m, 3H), 2.95(s, 3H), 3.72(s, 3H), 3.8-3.95(m, 4H), 6.82(d, 1H), 7.32(m, 1H), 7.48(d, 1H), 7.55(m, 1H), 7.75(d, 1H), 7.78(m, 1H), 8.05(m, 1H), 8.18(m, 1H).

EXAMPLE 10

A mixture of 8-fluoro-1,2-dihydro-6-iodo-1-methylquinolin-2-one (0.2 g), 4-(3-mercaptophenyl)-4-methoxytetrahydropyran (0.148 g), cuprous chloride (0.02 g), potassium carbonate (0.148 g) and DMF (0.74 ml) was heated to 140° C. for 2 hours. The mixture was cooled to ambient temperature and partitioned between ethyl acetate and water. The organic phase was washed with water, N aqueous sodium hydroxide solution, water and brine, dried (MgSO$_4$) and evaporated. The residue was purified by column chromatography using increasingly polar mixtures of hexane and ethyl acetate as eluent. There was thus obtained 4-[3-(8-fluoro-1,2-dihydro-1-methyl-2-oxoquinolin-6-ylthio)phenyl]-4-methoxytetrahydropyran (0.13 g, 50%), m.p. 104°–106° C.

The 8-fluoro-1,2-dihydro-6-iodo-1-methylquinolin-2-one used as a starting material was obtained as follows:

A solution of 8-fluoro-1,2-dihydro-1-methylquinolin-2-one (0.41 g; *Chem. Abs.*, 91, 175220c) in glacial acetic acid (2 ml) was stirred at ambient temperature and iodine (0.294 g), iodic acid (0.135 g) and concentrated sulphuric acid (0.23 ml) were added in turn. The resultant mixture was heated to 85° C. for 2.5 hours. The mixture was cooled to ambient temperature, methylene chloride (10 ml) was added and the mixture was neutralised by the addition of a saturated aqueous sodium bicarbonate solution. The mixture was washed with a saturated aqueous sodium sulphite solution and with brine, dried (MgSO$_4$) and evaporated. The residue, which comprised a mixture of the 6-iodo and 3,6-diiodo derivatives, was purified by column chromatography using increasingly polar mixtures of hexane and ethyl acetate as eluent. There was thus obtained the required starting material (0.21 g, 30%) as an oil.

NMR Spectrum (CDCl$_3$, δ values) 3.88(d, 3H), 6.72(d, 1H), 7.49–7.64(m, 3H).

EXAMPLE 11

Using a similar procedure to that described in Example 10, except that 1,2-dihydro-6-iodo-1,8-dimethylquinolin-2-one was used in place of 8-fluoro-1,2-dihydro-6-iodo-1-methylquinolin-2-one, there was obtained 4-[3-(1,2-dihydro-1,8-dimethyl-2-oxoquinolin-6-ylthio)phenyl]-4-methoxytetrahydropyran in 70% yield, m.p. 101°–102° C.

The 1,2-dihydro-6-iodo-1,8-dimethylquinolin-2-one used as a starting material was obtained as an oil, in 44% yield, using a similar procedure to that described in the portion of Example 10 which is concerned with the preparation of starting materials except that 1,2-dihydro-1,8-dimethylquinolin-2-one (*Chem. Abs.*, 89, 141987×) was used in place of 8-fluoro-1,2-dihydro-1-methylquinolin-2-one.

NMR Spectrum (CDCl$_3$, δ values) 2.68(s, 3H), 3.8(s, 3H), 6.65(d, 1H), 7.49(d, 1H), 7.61(d, 1H), 7.66(d, 1H).

EXAMPLE 12

Using a similar procedure to that described in Example 10, except that 1,2-dihydro-6-iodo-1-methylquinoxalin-2-one was used in place of 8-fluoro-1,2-dihydro-6-iodo-1-methylquinolin-2-one, there was obtained 4-[3-(1,2-dihydro-1-methyl-2-oxoquinoxalin-6-ylthio)phenyl]-4-methoxytetrahydropyran in 50% yield as a gum.

NMR Spectrum (CDCl$_3$, δ values) 1.85–2.1(m, 4H), 3.0(s, 3H), 3.7(s, 3H), 3.8(m, 4H), 7.25–7.85(m, 7H), 8.3(s, 1H).

The 1,2-dihydro-6-iodo-1-methylquinoxalin-2-one used as a starting material was obtained as follows:

A mixture of 1,2-phenylenediamine (10.8 g), chloroacetic acid (9.45 g) and sodium hydroxide pellets (8.0 g) was heated gently with a hot-air gun until the reactants began to melt. After 5 minutes the mixture was heated to 105° C. for 30 minutes. The mixture was cooled to ambient temperature and extracted with hot ethanol. The solution was filtered and evaporated. The residue was purified by column chromatography using ethyl acetate as eluent. There was thus obtained 1,2,3,4-tetrahydroquinoxalin-2-one (4.6 g, 32%), m.p. 133°–135° C.

A mixture of a portion (4 g) of the product so obtained, hydrogen peroxide (30% w/v, 4.2 ml) and 2N aqueous sodium hydroxide solution (55 ml) was heated to 100° C. for 1 hour. The mixture was cooled to ambient temperature and acidified to pH2 by the addition of concentrated hydrochloric acid. The precipitate which was deposited was filtered off, washed with water and dried. There was thus obtained 1,2-dihydroquinoxalin-2-one (3.2 g, 81%), m.p. 264° C.

Sodium hydride (55% w/w dispersion in mineral oil; 1 g) was added in portions to a solution of the product so obtained in DMF (150 ml) which had been cooled to 0° C. The mixture was stirred at ambient temperature for 2 hours. Methyl iodide (2 ml) was added and the mixture was stirred at ambient temperature for 16 hours. The mixture was evaporated and the residue was partitioned between ethyl acetate and water. The organic phase was washed with water and brine, dried (MgSO$_4$) and evaporated. The residue was purified by column chromatography using a 1:1 v/v mixture of toluene and ethyl acetate as eluent. There was thus obtained 1,2-dihydro-1-methylquinoxalin-2-one (2.24 g, 64%), m.p. 116°–118° C.

A solution of a portion (0.48 g) of the product so obtained in glacial acetic acid (2 ml) was stirred at ambient temperature and iodine (0.38 g), iodic acid (0.176 g) and concentrated sulphuric acid (0.3 ml) were added in turn. The resultant mixture was heated to 95° C. for 2 hours. The mixture was cooled to ambient temperature, methylene chloride (10 ml) was added and the mixture was neutralised by the addition of a saturated aqueous sodium bicarbonate solution. The mixture was washed with a saturated aqueous sodium sulphite solution and with brine, dried (MgSO$_4$) and evaporated. The residue was purified by column chromatography using a 1:1 v/v mixture of toluene and ethyl acetate as eluent. There was thus obtained the required starting material (0.16 g, 18%) as a solid.

Elemental Analysis: Found C, 38.0; H, 2.4; N, 9.5; C$_9$H$_7$N$_2$IO requires C, 37.8; H, 2.45; N, 9.8%.

EXAMPLE 13

The following illustrate representative pharmaceutical dosage forms containing the compound of formula I, or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph. Eur | 223.75 |
| | Croscarmellose sodium | 6.0 |
| | Maize starch | 15.0 |
| | Polyvinylpyrrolidone (5% w/v paste) | 2.25 |

-continued

| (b) | Tablet II | mg/tablet |
|---|---|---|
| | Magnesium stearate | 3.0 |

| (c) | Tablet III | mg/tablet |
|---|---|---|
| | Compound X | 1.0 |
| | Lactose Ph. Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph. Eur | 488.5 |
| | Magnesium stearate | 1.5 |

| (e) | Injection I | (50 mg/ml) |
|---|---|---|
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1M Sodium hydroxide solution | 15.0% v/v |
| | Water for injection to 100% | |

| (g) | Injection III | (1 mg/ml, buffered to pH6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |

-continued

| (j) | Aerosol III | mg/ml |
|---|---|---|
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

Note

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

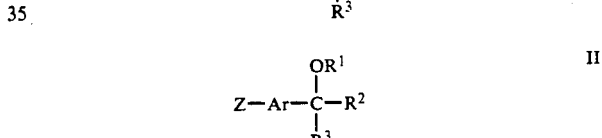

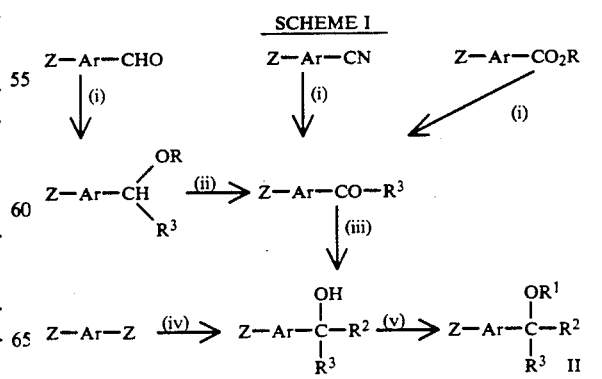

Reagents

-continued
SCHEME I (i) R³Li or R³MgZ, THF
(ii) DDQ or MnO₂
(iii) R²Li or R²MgZ, THF;
(iv) BuLi or Mg, THF; R²COR³, THF
(v) R¹Z, base
Note R = (1-4C)alkyl such as Me or Et

SCHEME II

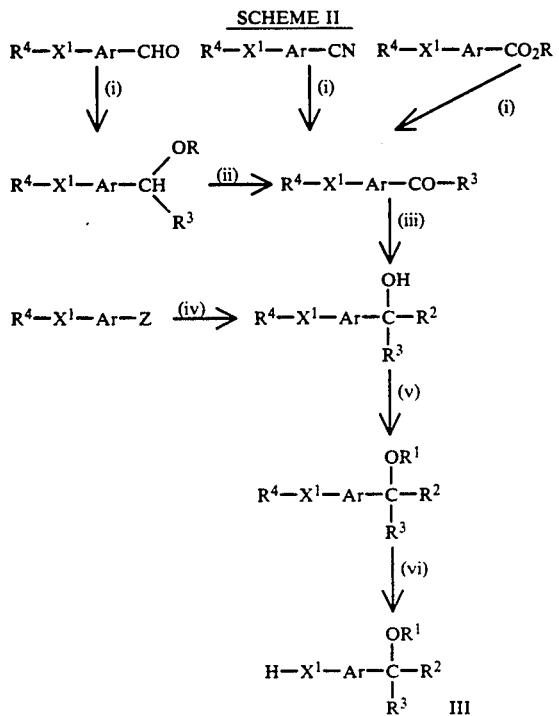

Reagents
(i) to (v) as in Scheme I
(vi) Conventional removal of the protecting group R⁴ which is, e.g, COMe, THP, CH₂Ph or Me.

SCHEME III

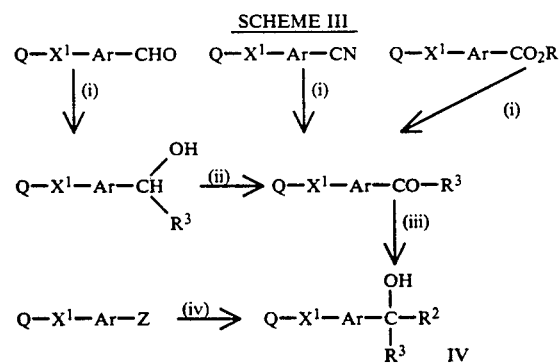

Reagents
(i) to (iv) as in Scheme I

What we claim is:
1. A heterocyclic derivative of the formula I

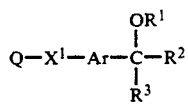

wherein Q is quinoxalinyl or a hydrogenated derivative thereof which may optionally bear one, two or three substituents selected from halogeno, hydroxy, oxo, carboxy, cyano, amino, (1-4C)alkyl, (1-4C)alkoxy, fluoro-(1-4C)alkyl, (1-4C)alkylamino, di-[(1-4C)alkyl]amino, hydroxy-(1-4C)alkyl, amino-(1-4C)alkyl, (1-4C)alkylamino-(1-4C)alkyl, di-[(1-4C)alkyl]amino-(1-4C)alkyl, amino-(2-4C)alkoxy, (1-4C)alkylamino-(2-4C)alkoxy and di-[(1-4C)alkyl]amino-(2-4C)alkoxy;

wherein $X^1$ is oxy, thio, sulphinyl, sulphonyl or imino;

wherein Ar is 1,3- or 1,4-phenylene which may optionally bear one or two substituents selected from halogeno, hydroxy, amino, nitro, cyano, carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino;

wherein $R^1$ is (1-6C)alkyl, (3-6C)alkenyl or (3-6C)alkynyl; and wherein $R^2$ and $R^3$ together form a group of the formula —$A^2$—$X^2$—$A^3$— which, together with the carbon atom to which $A^2$ and $A^3$ are attached, defines a ring having 6 ring atoms, wherein $A^2$ and $A^3$, which may be the same or different, each is (1-4C)alkylene, and $X^2$ is oxy, and which ring may bear one, two or three substituents, which may be the same or different, selected from halogeno, hydroxy, (1-4C)alkyl, (1-4C)alkoxy and fluoro-(1-4C)alkyl; or a pharmaceutically-acceptable salt thereof.

2. A heterocyclic derivative of the formula I as claimed in claim 1 wherein

Q is 2-quinoxalinyl, or 6-quinoxalinyl, which may optionally bear one, two or three substituents selected from fluoro, chloro, hydroxy, oxo, cyano, methyl, ethyl, propyl, methoxy, trifluoromethyl, 2-fluoroethyl, 2,2,2-trifluoroethyl, 2-aminoethyl, 2-methylaminoethyl and 2-dimethylaminoethyl;

$X^1$ is thio, sulphinyl, sulphonyl or imino;

Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido;

$R^1$ is methyl, ethyl, allyl or 2-propynyl; and $R^2$ and $R^3$ together from a group of the formula —$A^2$—$X^2$—$A^3$ which, together with the carbon atom to which $A^2$ and $A^3$ are attached, defines a ring having 6 ring atoms, wherein $A^2$ and $A^3$, which may be the same or different, each is methylene, ethylene, trimethylene or tetramethylene and $X^2$ is oxy, and which ring may bear one or two substituents selected from fluoro, hydroxy, methyl, ethyl, propyl, methoxy, ethoxy and trifluoromethyl; or a pharmaceutically-acceptable salt thereof.

3. A heterocyclic derivative of the formula I as claimed in claim 1 wherein

Q is 6-quinoxalinyl which may optionally bear one or two substituents selected from fluoro, chloro, methyl, ethyl, trifluoromethyl, 2-fluoroethyl and 2-dimethylaminoethyl;

$X^1$ is thio, sulphinyl or sulphonyl;

Ar is 1,3-phenylene or 1,4-phenylene which may optionally bear one or two substituents selected from fluoro, hydroxy, amino, nitro, ureido, methoxy, dimethylamino, trifluoromethyl and acetamido;

$R^1$ is methyl, ethyl, allyl or 2-propynyl; and $R^2$ and $R^3$ together form a group of the formula $-A^2-X^2-A^3-$ which, together with the carbon atom to which $A^2$ and $A^3$ are attached, defines a ring having 6 ring atoms, wherein $A^2$ is ethylene, $A^3$ is methylene or ethylene, and $X^2$ is oxy, and which ring may bear one or two substituents selected from fluoro, methyl, ethyl, propyl, methoxy and trifluoromethyl;

or a pharmaceutically-acceptable salt thereof.

4. A heterocyclic derivative of the formula I as claimed in claim 1 wherein

Q is 1,2-dihydro-2-oxoquinoxalin-6-yl which may optionally bear one or two substituents selected from fluoro, methyl, ethyl and 2,2,2-trifluoroethyl;

$X^1$ is thio, sulphinyl or sulphonyl;

Ar is 1,3-phenylene which may optionally bear one fluoro substituent;

$R^1$ is methyl; and $R^2$ and $R^3$ together form a group of the formula $-A^2-X^2-A^3-$ which together with the carbon atom to which $A^2$ and $A^3$ are attached, defines a ring having 6 ring atoms, wherein $A^2$ is ethylene, $A^3$ is ethylene and $X^2$ is oxy, and which ring may bear a methyl substituent;

or a pharmaceutically-acceptable salt thereof.

5. A pharmaceutical composition which comprises a heterocyclic derivative of the formula I, or a pharmaceutically-acceptable salt thereof, as claimed in claim 1 in association with a pharmaceutically-acceptable diluent or carrier.

6. A heterocyclic derivative of the formula I, or a pharmaceutically-acceptable salt thereof, as claimed in claim 1 for use in a method of treatment of the human or animal body by therapy.

7. A method of treating a disease or medical condition mediated alone or in part by one or more leukotrienes which comprises administering to a warm-blooded animal requiring such treatment an effective amount of a heterocyclic derivative of the formula I, or a pharmaceutically-acceptable salt thereof, as claimed in claim 1.

8. A pharmaceutical composition which comprises a heterocyclic derivative of the formula I, or a pharmaceutically-acceptable salt thereof as claimed in claim 1, in conjunction or admixture with a cyclooxygenase inhibitory non-steroidal anti-inflammatory agent, and a pharmaceutically-acceptable diluent or carrier.

* * * * *